United States Patent
Maris

(10) Patent No.: US 6,191,855 B1
(45) Date of Patent: *Feb. 20, 2001

(54) APPARATUS AND METHOD FOR THE DETERMINATION OF GRAIN SIZE IN THIN FILMS

(75) Inventor: Humphrey J Maris, Barrington, RI (US)

(73) Assignee: Brown University Research Foundation, Providence, RI (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/524,034

(22) Filed: Mar. 13, 2000

Related U.S. Application Data

(63) Continuation of application No. 09/110,886, filed on Jul. 7, 1998, now Pat. No. 6,038,026.

(51) Int. Cl.⁷ .................................................... G01B 9/02
(52) U.S. Cl. ........................ 356/357; 356/359; 356/35.5
(58) Field of Search .................................. 356/345, 357, 356/35.5, 359, 360

(56) References Cited

U.S. PATENT DOCUMENTS

| | | | |
|---|---|---|---|
| 4,484,820 | 11/1984 | Rosencwaig | 374/6 |
| 4,522,510 | 6/1985 | Rosencwaig et al. | 374/7 |
| 4,579,463 | 4/1986 | Rosencwaig et al. | 374/57 |
| 4,632,561 | 12/1986 | Rosencwaig et al. | 356/432 |
| 4,636,088 | 1/1987 | Rosencwaig et al. | 374/5 |
| 4,679,946 | 7/1987 | Rosencwaig et al. | 374/5 |
| 4,710,030 | 12/1987 | Tauc et al. | 356/432 |
| 4,750,822 | 6/1988 | Rosencwaig et al. | 356/445 |
| 4,795,260 | 1/1989 | Schuur et al. | 356/400 |
| 4,854,710 | 8/1989 | Opsal et al. | 356/432 |
| 4,952,063 | 8/1990 | Opsal et al. | 356/432 |
| 4,999,014 | 3/1991 | Gold et al. | 356/382 |
| 5,042,951 | 8/1991 | Gold et al. | 356/369 |
| 5,042,952 | 8/1991 | Opsal et al. | 356/432 |
| 5,074,669 | 12/1991 | Opsal | 356/445 |
| 5,546,811 | 8/1996 | Rogers et al. | 73/800 |
| 5,671,042 | * 9/1997 | Sciammarella | 356/35.5 |

OTHER PUBLICATIONS

B. M. Clemens et al., "Relationship between interfacial strain and the elastic response of multilayer metal films", Physical Review Letter, vol. 61, No. 20, Nov. 14, 1988.

G. Tas et al., "Picosecond Ultrasonic Investigation of Thin Interfacial Layers Between Films and a Substrate", IBM T. J. Watson Research Center.

P. A. Elzinga et al., "Pump/probe method for fast analysis of visible spectral signatures utilizing asynchronous optical sampling", Appl. Optics vol. 26, No. 19 Oct. 1, 1987.

R. J. Kneisler et al., "Asynchronous optical sampling: a new combustion diagnostic for potential use in turbulent, high-pressure flames", 1989 Optics Letters, vol 14, No. 5.

C. A. Paddock et al., "Transient Thermoreflectance From Thin Metal Films", J. Appl. Phys. 60, Jul 1, 1986.

D. M. Pennington et al., "Direct Measurement of the Thermal Expansion of a Surface Using Transient Gratings", Optical Society.

(List continued on next page.)

Primary Examiner—Robert Kim
(74) Attorney, Agent, or Firm—Ohlandt, Greeley, Ruggiero & Perle, L.L.P.

(57) ABSTRACT

A method for the determination of grain size in a thin film sample comprising the steps of measuring first and second changes in the optical response of the thin film, comparing the first and second changes to find the attenuation of a propagating disturbance in the film and associating the attenuation of the disturbance to the grain size of the film. The second change in optical response is time delayed from the first change in optical response.

8 Claims, 11 Drawing Sheets

OTHER PUBLICATIONS

K. A. Svinarich et al., "Picosecond Acoustic Pulse REflection From A Metal–Metal Interface", Dept. of Physics, Wayne State University.

G. L. Eesley et al., Generation and Detection of Picosecond Acoustic Pulses in Thin Metal Films, Appl. Phys. Lett. 50, Mar. 23, 1987.

G. J. Flechtner et al., "Measurements of Atomic Sodium in Flames by Asynchronous Optical Sampling: theory and experiment", Applied Optics, vol. 31, No. 15, May 20, 1992.

O. B. Wright, "Thickness and sound velocity measurement in thin transparent films with laser picosecond acoustics", Journal of Applied Physics, vol. 71, #4, Feb. 15, 1992.

O. B. Wright, et al. "High Resolution Laser Picosecond Acoustics in Thin Films" Symp. on Physical Acoustics, Belgium, 1990.

"Picosecond optical studies of amorphous diamond and diamondlike carbon: Thermal conductivity and longitudinal sound velocity", Christopher J. Morath, et al, J. Appl. Phys., vol. 76, No. 5, Sep. 1, 1994, p. 2636.

"Study of vibrational modes of gold nanostructures by picosecond ultrasonics", H. N. Lin, et al., J. Appl. Phys. vol. 73, No. 1, Jan. 1, 1993.

"Nondestructive detection of titanium disilicide phase transofrmation by picosecond ultrasonics", H. N. Lin, et al., Applied Physics Letters, No. 61, p. 2700, 1992.

O. B. Wright et al. "Laser Picosecond Acoustics in Various Types of Thin Film", Japanese Journal of Applied Physics, vol. 31, (1992).

Attenuation of longitudinal–acoustic phonons in amorphous $SiO_2$ at frequencies up to 440 $GH_z$, T. C. Zhu, et al., The American Physical Society 1991.

"Detection of Titanium Silicide Formation And Phase Transformation by Picosecond Ultrasonics", H. N. Lin, et al., Mat. Res. Soc. Proc. Advanced Metalization and Processing for Semiconductor Devices III, vol. 260, p. 221 (1992).

"Ultrasonic Experiments At Ultra–High Frequency With Picosecond Time–Resolution", H. N. Lin, et al., IEEE Ultrasonics Symp. 90.

"Picosecond Optics Studies Of Vibrational And Mechanical Properties of Nanostructures", H. J. Maris, et al., AMD–vol. 140, Acousto–Optics and Acoustic Microscopy ASME 1992.

"Time–resolved study of vibrations of a–Ge:H/a–Si:H multilayers", H. T. Grahn, et al Physical Review B, vol. 38, No. 9, Sep. 15, 1988.

"Picosecond Ultrasonics", Holger T. Grahn, et al., IEEE Journal of Quantum Electronics, vol. 25, No. 12, Dec. 1989.

Nondestructive Testing of Microstructures by Picosecond Ultrasonics, H. N. Lin, et al., Journal of Nondestructive Evaluation, vol. 9, No. 4, 1990.

"Phonon Attenuation and Velocity Measurements in Transparent Materials by Picosecond Acoustic Interferometry", H. N. Lin, et al. Journal of Applied Physics, vol. 69, p. 3860 (Apr. 1991).

"Studies of High–Frequency Acoustic Phonons Using Picosecond Optical Techniques", H. J. Maris, et al., Phonon Scattering in Condensed Matter 5, Eds. A. C. Anderson, J. C. Wolfe, Springer, Berlin, 1986, p. 374.

"Picosecond Photoinduced Electronic And Acoustic Effects In a–Si:H Based Multilayer Structures", H. T. Grahn, et al., Journal of Non–Crystalline Solids 97&98 (1987) pp. 855–858.

"Picosecond Acoustics As A Non–Destructive Tool For The Characterization Of Very Thin Films", C. Thomsen, et al., Thin Solid Films, 154 (1987) pp. 217–223.

"Noninvasive picosecond ultrasonic detection of ultrathin interfacial layers: CFx at the Al/Si interface" by G. Tas, R. J. Stoner and H. J. Maris, Appl Phys. Lett. 61 (15). Oct. 12, 1992 pp. 1787–1789.

"Detection Of Thin Interfacial Layers By Picosecond Ultrasonics" by G. Tas, R. J. Stoner J. Maris, G. W. Rubloff, G. S. Oehrlein and J. M. Halbout, Mat. Res. Soc. Symp. Proc. vol. 259 1992 Materials Research Society, pp. 231 236.

"Surface Generation and Detection of Phonons By Picosecond Light Pulses" C. Thomsen et al. Physical Review B. vol. 34, No. 6, Sep. 15, 1986, The American Physical Society, pp. 4129–4138.

"Sound Velocity and Index of Refraction of AIAs Measured By Picosecond Ultrasonics", H. T. Grahn, et al. Appl. Phys. Lett. 53(21), Nov. 21, 1988 pp. 2023–2024.

"Elastic Properties of Silicon Oxynitride Films Determined by Picosecond Acoustics" by H. T. Grahn et al., Appl. Phys. Lett. 53 (23), Dec. 5, 1988, pp. 2281–2283.

D. A. Young et al. "Heat Flow in Glasses on a Picosecond Timescale". Dept. of Engineering, Brown University, Providence, RI. 1986. pp. 49–51.

S. Sumie et al. "A New Method of Photothermal Displacement Measurement by Laser Interferometric Probe". Jpn. J. Appl. Phys. vol. 31 Pt. 1, No. 11, 1992 pp. 3575–3583.

S. Sumie et al. J. Appl. Phys. 76(10), Nov. 15, 1994 pp. 5681–5689.

F. E. Doany et al. "Carrier lifetime versus ion–implantation dose in silicon on sapphire". Appl. Phys. Lett. 50(8), Feb. 23, 1987 pp. 460–462.

D. H. Auston et al. "Picosecond Ellipsometry of Transient Electron–Hole Plasmas in Germanium". Physical Review Letters, vol. 32 No. 20. May 20, 1974 pp. 1120–1123.

R. J. Stoner et al. "Kapitza conductance and heat flow between solids at temperatures from 50 to 300 K". Physical Review B, vol. 48, No. 22, Dec. 1, 1993 pp. 16 373–16 387.

R. J. Stoner et al. "Measurements of the Kapitza Conductance between Diamond and Several Metals". Physical Review Letters, vol 68 No. 10, Mar. 9, 1992 pp. 1563–1566.

A. Rosencwaig et al. "Detection of thermal waves through optical reflectance". Appl. Phys. Lett., vol. 46 No. 11, Jun. 1, 1985. pp. 1013–1015.

A. Elci et al. "Physics of Ultrafast Phenomena in Solid State Plasmas". Solid–State Electronics, vol. 21, 1978, pp. 151–158.

D. H. Auston et al. "Picosecond Spectroscopy of Semiconductors". Solid–State Electronics, vol. 21, 1978, pp. 147–150.

W. Lee Smith et al. "Ion implant monitoring with thermal wave technology". Appl. Phys. Lett.. vol. 47. No. 6, Sep. 15, 1985. pp. 584–586.

J. Opsal et al. "Thermal and plasma wave depth profiling in silicon". Appl. Phys.Lett. vol. 47 No. 5, Sep. 1, 1985. pp. 498–500.

A. Rosencwaig et al. "Thin–film thickness measurements with thermal waves". Appl. Phys. Lett., vol. 43 No. 2, Jul. 15, 1983. pp. 166–168.

* cited by examiner

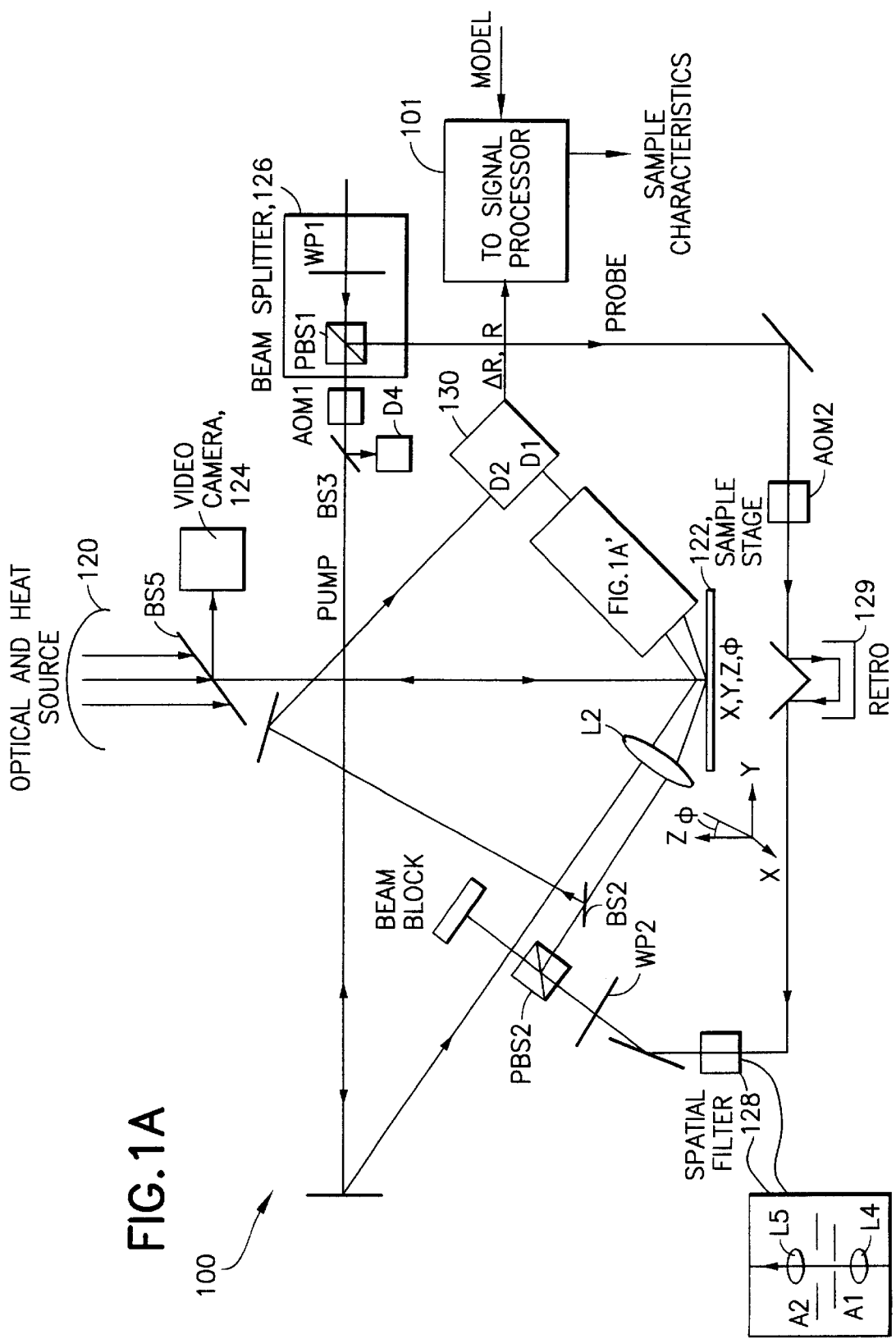

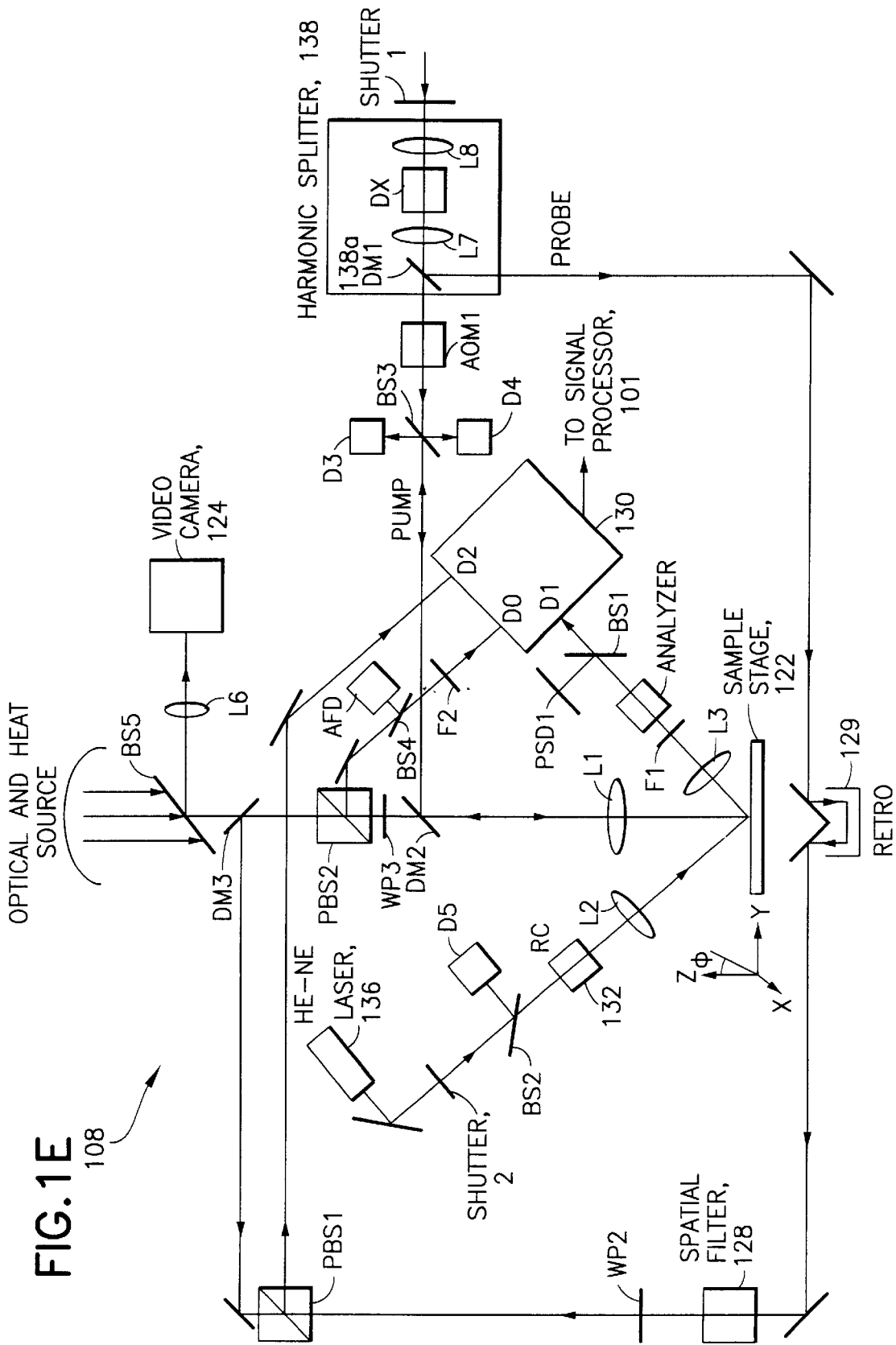

APPARATUS AND METHOD FOR THE DETERMINATION OF GRAIN SIZE IN THIN FILMS

CROSS-REFERENCE TO A RELATED PATENT APPLICATION

This patent application is related to U.S. patent application Ser. No. 08/924,792 filed Feb. 25, 1998, entitled "Ultrafast Optical Technique for the Characterization of Altered Materials", which is continuation in part of U.S. patent application Ser. No. 08/519,666 filed Aug. 25, 1985 now U.S. Pat. No. 5,706,094 dated Jan. 6, 1998.

This patent application is a continuation of copending and allowed U.S. patent application Ser. No. 09/110,886, filed Jul. 7, 1998, now U.S. Pat. No. 6,038,026, issued Mar. 14, 2000, the disclosure of which is incorporated by reference herein in its entirety.

STATEMENT OF GOVERNMENT RIGHTS

This invention was made with Government support under Contract No. DE-FG02-86ER45267 awarded by the Department of Energy. The Government has certain rights in this invention.

FIELD OF THE INVENTION

This invention relates generally to a method for characterizing a sample composed of one or more thin films through the use of electromagnetic radiation to generate and detect stress or strain pulses. The grain size in the sample is determined from measurements of the propagation characteristics of the strain pulses in the sample.

BACKGROUND OF THE INVENTION

Currently, in the semiconductor industry there is a great interest in the characterization of thin films. Integrated circuits are made up a large number of thin films deposited onto a semiconductor substrate, such as silicon. The thin films include metals to make connections between the transistors making up the chip, and dielectric films to provide insulation between the metal layers (see: S. A. Campbell, The Science and Engineering of Microelectronic Fabrication, Oxford University Press, (1996)). The metal films (interconnects) are typically arranged as a series of patterned layers. At the present time there may be 4 or 5 layers of interconnects. It is likely that as more complex integrated circuits are developed which will require a greater number of interconnections the number of layers will increase. Metals of current interest include, for example, aluminum, copper, titanium and suicides. Insulating films include, for example, oxide glasses of various compositions and polymers.

A metal film will contain crystal grains with a distribution of sizes and orientations. The range of sizes may be narrow or broad, and a distribution of grain sizes may have a maximum at some size and then decrease monotonically as the size increases or decreases. Alternatively, there may be a bi-modal distribution so that there is a high concentration of grains in two different ranges of size. The grain size affects the mechanical and electrical properties of a metal film. Consequently, in the semiconductor industry there is a strong interest in finding techniques that can monitor the grain size in metal films.

In the semiconductor device fabrication industry, it is important that a method for grain size determination be non-destructive, be able to measure the grain size within a small area of film, and give results in a short period of time. Current techniques for the determination of grain size include; measurement of the width of the peaks in intensity of diffracted X-rays, electron microscopy and atomic force and scanning tunneling microscopy. These techniques cannot meet the combined requirements listed above.

OBJECTS OF THE INVENTION

It is a first object of the invention to provide a method for the determination of grain size in films through the use of an optical metrology technique employing a short optical pulse to generate a mechanical strain pulse and a second optical pulse to detect the propagation of the strain pulse. From the measured characteristics of the detected strain pulse the grain size is determined.

It is a further object of the invention to provide a means for the determination of both the grain size and information about the distribution of grain orientations.

SUMMARY OF THE INVENTION

In accordance with a method of the present invention, a method for the determination of grain size in a thin film sample is provided. The method comprises the steps of measuring a first change in optical response and a second change in the optical response of the thin film, comparing the first and second changes to find the attenuation of a propagating disturbance in the film, and associating the attenuation of the disturbance to the grain size of the film. The second change in optical response is time delayed from the first change in optical response.

In accordance with a first embodiment of the present invention, a metal film grain size measuring system is provided. The measuring system comprises a stage holding a substrate having the metal film, means for applying a non-destructive optical pump pulse and a non-destructive optical probe pulse to the metal film, means for detecting changes in the probe pulse, means for defining the detected changes in the probe pulse and means for relating the changes in the probe pulse to the grain size of the metal film. The substrate has the metal film disposed on a first side thereof. The pump pulse and probe pulse are applied to a free surface of the thin film. The probe pulse is temporally delayed from the pump pulse. The means for detecting detect changes in the probe pulse reflected from the metal film. The detecting means detect the change in the probe pulse as a function of time. The means for defining define the detected changes in the probe pulse as a function of frequency. The means for relating relate the changes in the probe pulse defined as a function of frequency to a grain size of the metal film.

In accordance with a second method of the present invention, a method for determining the grain size in a sample is provided. The method comprises the steps of measuring a first change in optical response of the sample, comparing the first change in optical response to a calculated ideal optical response to determine the attenuation of a propagating disturbance in the sample and relating the attenuation of the propagating disturbance in the sample to the grain size of the sample.

BRIEF DESCRIPTION OF THE DRAWINGS

The above set forth and other features of the invention are made more apparent in the ensuing Detailed Description of the Invention when read in conjunction with the attached Drawings, wherein:

FIG. 1A' illustrates a portion of FIG. 1A in greater detail;

FIG. 1E is a block diagram of a fifth embodiment of an ultra-fast optical system that is suitable for use in practicing this invention, specifically, a dual wavelength, normal incidence pump and probe, combined ellipsometer embodiment;

DETAILED DESCRIPTION OF THE INVENTION

Figure 1A:
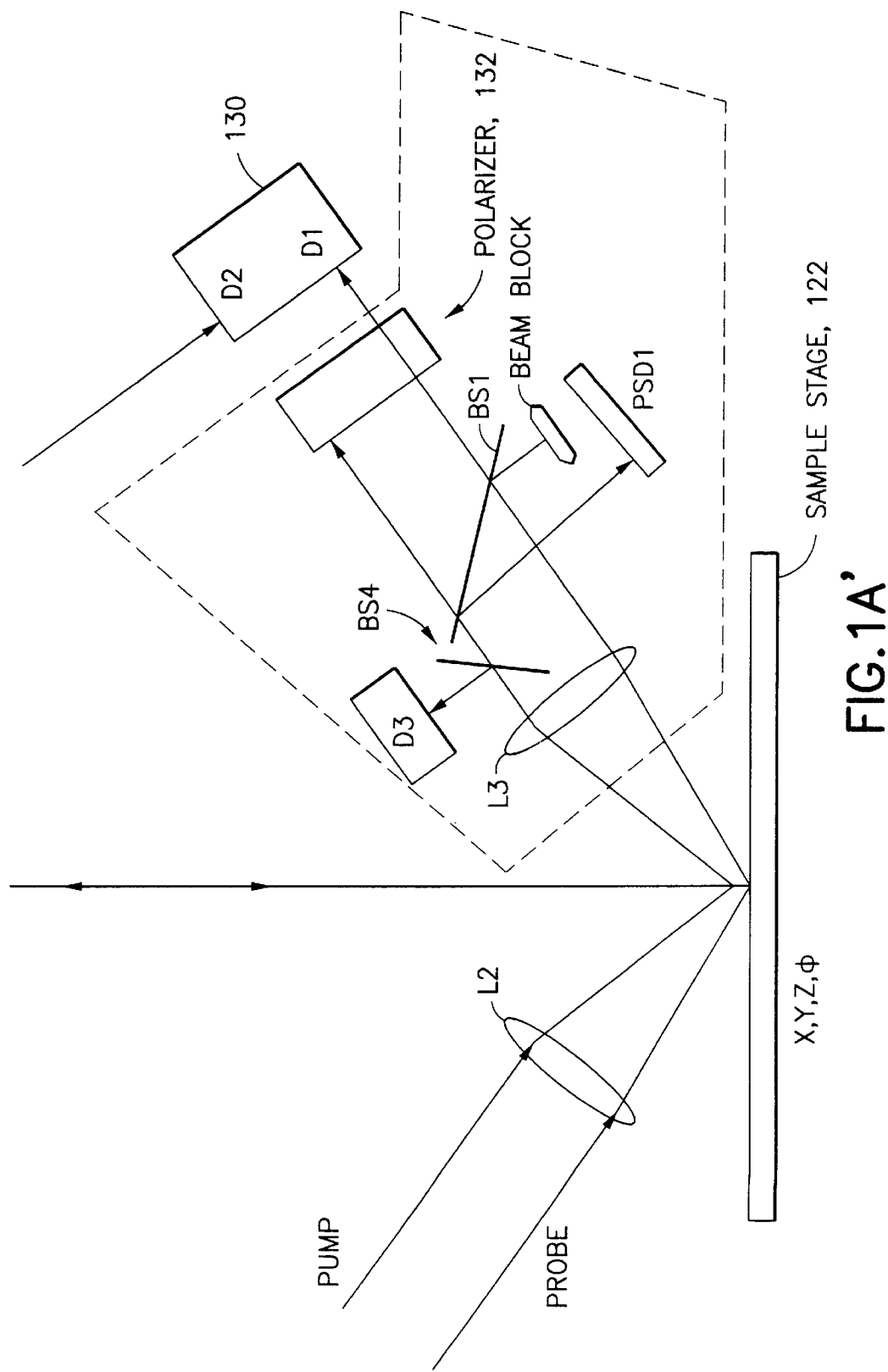
FIG. 1A is a block diagram of a first, embodiment of an ultra-fast optical system that is suitable for use in practicing this invention, specifically, a parallel, oblique beam embodiment.

The teaching of this invention is practiced at least in part with an optical generator and a detector of a stress wave within a sample. The sample is comprised of a substrate having at least one metal film deposited thereon. The metal film may be made of copper or aluminum or any other suitable material. The thickness of the film could range from 100 Å to 10µ. In this system, a non-destructive first light pulse is directed onto the sample. This first light pulse, referred to hereafter as a pump beam, is absorbed in a thin layer at the top surface of the sample. When the pump beam is absorbed, the temperature of the surface layer is increased, and the layer tries to expand. This launches a strain pulse which propagates into the film. When the strain pulse reaches the film-substrate interface, a part of the strain pulse is reflected back towards the top surface of the film. When the strain pulse reaches the top surface of the film, the change in strain associated with the propagating pulse results in a change in the optical constants of the metal. This change leads to a sudden change ΔR(t) in the optical reflectivity R of the top surface of the metal film. This change is measured by means of a second light pulse directed at the sample. This second light pulse, referred to hereafter as a probe beam, is time-delayed relative to the pump beam. Upon reaching the top surface of the film, the propagating strain pulse is reflected from the top surface towards the substrate and then a second time from the film-substrate interface back again towards the top surface. The change in ΔR(t) in the optical reflectivity in the top surface of the film associated with the strain pulse again reaching the top surface is again measured by means of the probe beam. The grain size and grain orientation of the film material are measured by observing the decay of the changes in the reflected probe beam.

In bulk materials the measurement of ultrasonic attenuation is an established method for the determination of grain size (U.S. Pat. No. 4,026,157 and U.S. Pat. No. 4,539,848). In a polycrystalline material a propagating ultrasonic wave is scattered because of the elastic anisotropy of the crystal grains. The theory of this scattering was worked out by E. M. Lifshitz and G. D. Parkhomovskii, Soviet Journal of Experimental and Theoretical Physics, Vol. 20, 175–182 (1950) (hereinafter, Lifshitz and Parkhomovskii), and was further developed by L. G. Merkulov, Soviet Journal of Technical Physics 26, 64–75 (1956) (hereinafter, Merkulov). For crystallites of cubic symmetry the scattering of the sound results in an attenuation a which for a longitudinal sound wave is given by the formula:

$$\alpha = \frac{8\pi^3 \mu^2 T f^4}{375 \rho^2 v^8}(2 + 3\gamma^5) \quad (1)$$

where $\mu = c_{11} - c_{12} - 2c_{44}$;

$c_{11}$, $c_{12}$, and $C_{44}$ are second order elastic constants of the material;

T is the volume of the grain;

f is the frequency for the sound;

ρ is the mass density;

v is the velocity of longitudinal sound;

γ is the ratio of the longitudinal sound velocity to the transverse sound velocity.

The quantity μ measures the degree of elastic anisotropy of the material. If μ=0 then the attenuation of the ultrasonic wave by grain scattering is zero. Equation 1 holds only if the ultrasonic wavelength is significantly larger than the grain size. The condition is usually given more precisely as:

$$\lambda \geq 2\pi D_{av} \quad (2)$$

where λ is the wavelength, and $D_{av}$ is the average grain diameter. If the λ is less than $2\pi D_{av}$ then the attenuation is given by the expression:

$$\alpha = \frac{16\pi^2 \mu^2 D_{av} f^2}{525 v^6 \rho^2} \quad (3)$$

For very short wavelengths such that $\lambda \ll D_{av}$, the attenuation ceases to vary with the frequency, and the attenuation is given by a different expression (W. P. Mason and H. J. McSkimin, J. Appl. Phys. 1, 940–946 (1948); L. G.

Merkulov, Sov. J. Tech. Physics, 2, 953–957 (1957)). For crystals which are not of cubic symmetry corresponding expressions for the attenuation have been derived (Lifshitz and Parkhomovskii, and Merkulov).

These theoretical expressions are based on a number of assumptions. One assumption is that the grains in the thin film are randomly oriented (i.e. there is no preferred orientation). The effect of preferred orientation is to reduce the magnitude of the attenuation. For example, if all the grains have the same orientation the attenuation will be zero. It is possible to calculate the reduction of attenuation that results from preferred orientation (E. P. Papadakis, Journal of Applied Physics 36, 1738–1740 (1965)). Even when there is significant preferred orientation of the grains there will still be a transition between a lower frequency range in which the attenuation varies as $f^4$ to a higher frequency range in which the attenuation varies as $f^2$. The frequency at which this transition occurs corresponds to the ultrasonic wavelength matching the quantity $2\pi D_{av}$. A second assumption underlying Eqs. 1 and 3 is that the grains are equiaxed (i.e. have a roughly spherical shape). A third assumption is that the range of grain sizes about the average value $D_{av}$ is small. If this is not true it is possible to arrive at an effective average grain size for use in these equations (E. P. Papadakis, in Physical Acoustics, edited by W. P. Mason, Vol. IV part B, 269–328 (1968)). This effective average grain size is dependent on the functional form of the distribution of grain size that is believed to exist in the material. Finally, the elastic anisotropy is assumed to be small (i.e. the variation of the sound velocity with crystal direction is assumed to be significantly less than sound velocity itself). Given the above assumptions, the grain size of a material is found by comparing the measured attenuation $\alpha$ of sound waves in the material at a discrete frequency to the theoretical formulas described in Eqs. 1 and 3. Furthermore, the attenuation $\alpha$ is measured for a range of frequencies in order to confirm the appropriate equation from Eqs. 1 and 3 to be used in relating the attenuation at the discrete frequency with the grain size of the material. For example, if it is found that the attenuation varies as the fourth power of the frequency this can be taken as a confirmation that the wavelength $\lambda$ is greater than $2\pi D_{av}$, and that it is appropriate to use Eq. 1 to determine the grain size from the measured attenuation $\alpha$.

For measurements on bulk materials it is, in many cases, sufficient to make ultrasonic measurements in the frequency range of 1 to 100 MHz. The reasons for this are essentially as follows. In ultrasonic experiments, it is straightforward to measure attenuation coefficients which are in a range such that there is appreciable attenuation over the ultrasonic path length. In measurements on bulk materials the ultrasound usually travels a distance of at least a few centimeters. Thus the magnitude of the attenuation coefficients $\alpha$ that are measured is typically in the range 0.1 to 10 cm$^{-1}$. If the attenuation is much less than the lower limit of this range the successive echoes have nearly the same amplitude. The attenuation is calculated from the small difference in these amplitudes, and the uncertainty in its determination becomes very large. On the other hand if the attenuation is larger than the upper limit then the ultrasonic wave is attenuated so much that it is hard to detect the wave after it has passed through the sample. The wavelength of ultrasound in a typical metal varies from 0.5 cm at 1 MHz to 0.005 cm at 100 MHz. The grain size in a bulk material may vary greatly depending on the material and according to the manner in which the material was prepared. However, for many bulk metals of technical interest it is found that within the frequency range 1 to 100 MHz there is a frequency interval over which the attenuation of ultrasound has a magnitude which is easy to measure.

These conventional ultrasonic techniques cannot be applied to the measurement of the grain size in thin polycrystalline films. One reasons for this is that in thin films the attenuation coefficient $\alpha$ has to have a very large value in order for there to be an appreciable attenuation during one pass of the sound through the film. For example, in a film of thickness 1 micron the attenuation coefficient has to be at least $10^3$ cm$^{-1}$ in order for the amplitude of the wave to be decreased by 10%. Another reason conventional ultrasonic techniques cannot be applied to thin films grain size measurement is that the grain size in thin films is typically significantly smaller than it is in bulk materials thereby giving a smaller attenuation. Consequently, to determine the grain size in thin films it is desirable to use a much higher frequency, as is achieved by the present invention, than is customary in conventional ultrasonic methods.

Reference is now made to FIG. 1A and FIG. 1A', collectively referred to below as FIG. 1A, for illustrating a first embodiment of an apparatus 100 suitable for practicing this invention. This embodiment is referred to as a parallel, oblique embodiment.

This embodiment includes an optical/heat source 120, which functions as a variable high density illuminator, and which provides illumination for a video camera 124 and a sample heat source for temperature-dependent measurements under computer control. An alternative heating method employs a resistive heater embedded in a sample stage 122. One advantage of the optical heater is that it makes possible rapid sequential measurements at different temperatures, or at one stabilized temperature.

The video camera 124 provides a displayed image for an operator, and facilitates the set-up of the measurement system. Appropriate pattern recognition software can also be used for this purpose, thereby minimizing or eliminating operator involvement. BS5 is a broad band beam splitter that directs video and a small amount of laser light to the video camera 124. The camera 124 and processor 101 can be used to automatically position the pump and probe beams on a measurement site.

Figure 4:
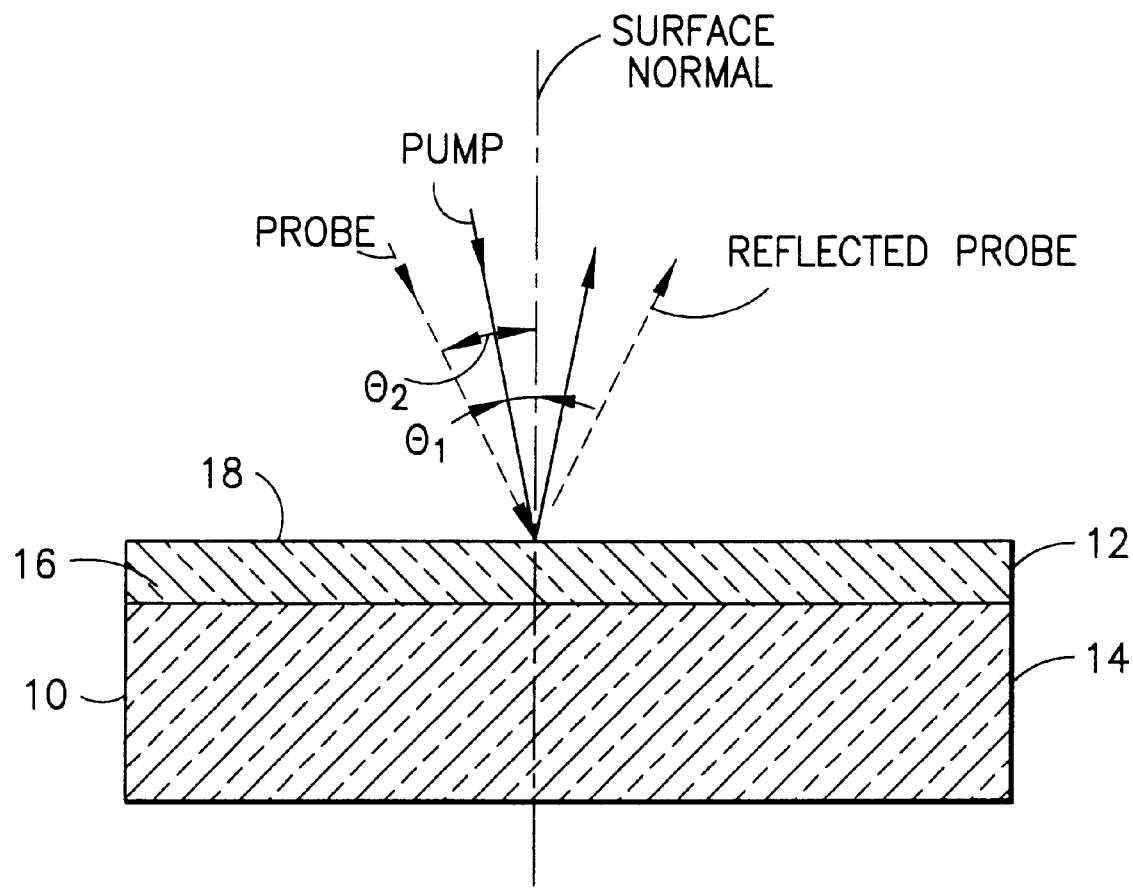
FIG. 4 is a schematic cross-sectional view of a sample thin film to be characterized in accordance with a first method of the invention.

The sample stage 122 holds a sample 10 comprising a thin film 12 deposited on a side 16 of the substrate 14 (see FIG. 4). The sample stage 122 is preferably a multiple-degree of freedom stage that is adjustable in height (global z-axis), position (global x and y-axes), and optionally tilt ($\phi$), and allows motor controlled positioning of a portion of the sample 10 relative to the pump and probe beams. The global z-axis is used to translate the sample 10 vertically into the focus region of the pump and probe, the global x and y-axes translate the sample parallel to the focal plane, and the tilt axes adjust the orientation of the stage 122 to establish a desired angle of incidence for the probe beam. This is achieved via position sensitive detector PSD1 and a signal processor 101, as described below.

In an alternative embodiment, the optical head may be moved relative to a stationary, tiltable stage (not shown). This is particularly important for scanning large objects (such as 300 mm diameter wafers, or mechanical structures, etc.) In this embodiment the pump beam, probe beam, and video signal can be delivered to or from the translatable head via optical fibers or fiber bundles.

The pump-probe beam splitter 126 splits an incident laser beam pulse (preferably of picosecond or shorter duration) into pump and probe beams, and includes a rotatable half-wave plate (WP1) that rotates the polarization of the unsplit beam. WP1 is used in combination with polarizing beam splitter PBS1 to effect a continuously variable split between pump and probe power. This split may be controlled by the computer by means of a motor to achieve an optimal signal to noise ratio for a particular sample. The appropriate split depends on factors such as the reflectivity and roughness of the sample. Adjustment is effected by having a motorized mount rotate WP1 under computer control.

A first acousto-optic modulator (AOM1) chops the pump beam at a frequency of about 1 MHz. A second acousto-optic modulator (AOM2) chops the probe beam at a frequency that differs by a small amount from that of the pump modulator AOM1. The use of AOM2 is optional in the system illustrated in FIG. 1A. Optionally, the AOMs may be synchronized to a common clock source, and may further be synchronized to the pulse repetition rate (PRR) of the laser that generates the pump and probe beams. Optionally an electro-optic modulator can be used in place of acousto-optic modulators AOM1 or AOM2.

A spatial filter 128 is used to preserve at its output a substantially invariant probe beam profile, diameter, and propagation direction for an input probe beam which may vary due to the action of the mechanical delay line shown as a retroreflector 129. The spatial filter 128 includes a pair of apertures A1 and A2, and a pair of lenses L4 and L5. An alternative embodiment of the spatial filter incorporates an optical fiber, as described above. If the profile of the probe beam coming from the mechanical delay line does not vary appreciably as the retroreflector 129 is moved, the spatial filter 128 can be omitted.

WP2 is a second adjustable halfwave plate which functions in a similar manner with PBS2 to the WP1/PBS1 combination of the beam splitter 126. The part of the beam passing through the beam splitter PBS1 impinges on a beam block. Beam splitter BS2 is used to direct a small fraction of the probe beam onto reference detector D2. The output of D2 is amplified and sent through a low pass filter to give an electrical signal LF2 which is proportional to the average intensity of the incident probe beam.

The probe beam after passing through BS2 is focused onto the sample by lens L2. After reflection from the sample the beam is collimated and after passing polarizer 132 is incident on photodetector D1. From the output of D1 two electrical signals are derived. The first signal LF1 is obtained by passing the amplified output of D1 through a low pass filter to give an electrical signal proportional to the average intensity of the incident probe beam. The second signal HF1 is obtained by passing the amplified output of D1 through a high pass filter which passes the frequency of modulation used for AOM1.

The low frequency signals LF1 and LF2 can be used to determine the reflectivity of the sample, after allowance is made for fixed losses in both optical paths. The signal LF2 and the average (dc) output of detector D4 give a measure of the intensity of the pump and probe beams. These signals are fed to a computer, for example the signal processor 101, which in turn controls motorized waveplates WP1 and WP2. The computer is programmed to adjust these waveplates so as to give the desired total optical power and pump/probe ratio for a sample exhibiting a particular reflectivity.

The linear polarizer 132 is employed to block scattered pump light polarization, and to pass the probe beam. The beamsplitter BS1 is used to direct a small part of the pump beam, and optionally a small part of the probe beam, onto a first Position Sensitive Detector (PSD1) that is used for autofocusing, in conjunction with the processor 101 and movements of the sample stage 122. The PSD1 is employed in combination with the processor 101 and the computer-controlled stage 122 (tilt and z-axis) to automatically focus the pump and probe beams onto the sample to achieve a desired focusing condition.

The detector D1 may be used in common for reflectometry, ellipsometry, and transient optical embodiments of this invention. However, the resultant signal processing is different for each application. For transient optical measurements, the DC component of the signal is suppressed, such as by subtracting reference beam input D2, or part of it as needed, to cancel the unmodulated part of D1, or by electrically filtering the output of D1 so as to suppress frequencies other than that of the modulation. The small modulated part of the signal is then amplified and stored. For ellipsometry, there is no small modulated part, rather the entire signal is sampled many times during each rotation of the rotating compensator (see discussion of FIG. 1B below), and the resulting waveform is analyzed to yield the ellipsometric parameters. For reflectometry, the change in the intensity of the entire unmodulated probe beam due to the sample is determined by using the D1 and D2 output signals (D2 measures a signal proportional to the intensity of the incident probe). Similarly, additional reflectometry data can be obtained from the pump beam using detectors D3 and D4. The analysis of the reflectometry data from either or both beams may be used to characterize the sample. The use of two beams is useful for improving resolution, and for resolving any ambiguities in the solution of the relevant equations.

A third beamsplitter BS3 is used to direct a small fraction of the pump beam onto detector D4, which measures a signal proportional to the incident pump intensity. A fourth beamsplitter BS4 is positioned so as to direct a small fraction of the pump beam onto detector D3, which measures a signal proportional to the reflected pump intensity.

Figure 1B:
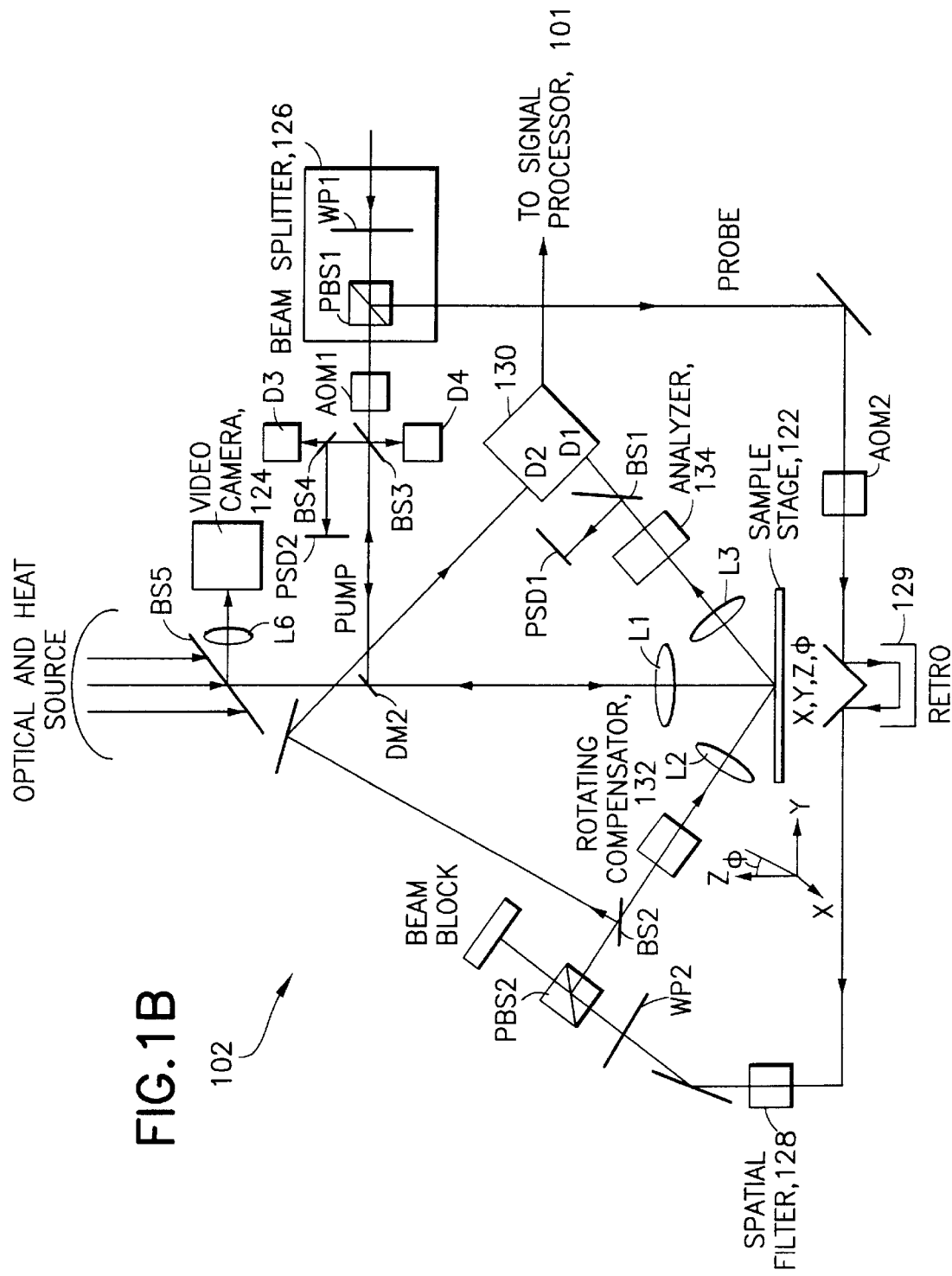
FIG. 1B is a block diagram of a second embodiment of an ultra-fast optical system that is suitable for use in practicing this invention, specifically, a normal pump, oblique probe embodiment.

FIG. 1B illustrates a normal pump beam, oblique probe beam embodiment of apparatus 102. Components labelled as in FIG. 1A function in a similar manner, unless indicated differently below. In FIG. 1B there is provided the above-mentioned rotating compensator 132, embodied as a linear quarter wave plate on a motorized rotational mount, and which forms a portion of an ellipsometer mode of the system. The plate is rotated in the probe beam at a rate of, by example, a few tens of Hz to continuously vary the optical phase of the probe beam incident on the sample. The reflected light passes through an analyzer 134 and the intensity is measured and transferred to the processor 101 many times during each rotation. The signals are analyzed according to known types of ellipsometry methods to determine the characteristics of the sample (transparent or semi-transparent films). This allows the (pulsed) probe beam to be used to carry out ellipsometry measurements.

The ellipsometry measurements are carried out using a pulsed laser, which is disadvantageous under normal conditions, since the bandwidth of the pulsed laser is much greater than that of a CW laser of a type normally employed for ellipsometry measurements.

The ellipsometry measurement capability is useful in performing certain of the embodiments of the method described below, wherein it is required to determine the index of refraction of a film layer disposed over a substrate.

If transient optical measurements are being made, the rotating compensator 132 is oriented such that the probe beam is linearly polarized orthogonal to the pump beam. The analyzer 134 may be embodied as a fixed polarizer, and also forms a portion of the ellipsometer mode of the system. When the system is used for transient optical measurements the polarizer 134 is oriented to block the pump.

The analyzer 134 may be embodied as a fixed polarizer, and also forms a portion of the ellipsometer mode of the system. When used in the ellipsometer mode, the polarizer 134 is oriented so as to block light polarized at 45 degrees relative to the plane of the incident and reflected probe beam.

The embodiment of FIG. 1B further includes a dichroic mirror (DM2), which is highly reflective for light in a narrow band near the pump wavelength, and is substantially transparent for other wavelengths.

It should be noted in FIG. 1B that BS4 is moved to sample the pump beam in conjunction with BS3, and to direct a portion of the pump to D3 and to a second PSD (PSD2). PSD2 (pump PSD) is employed in combination with the processor 101, computer controlled stage 122 (tilt and z-axis), and PSD1 (Probe PSD) to automatically focus the pump and probe beams onto the sample to achieve a desired focusing condition. Also, a lens L1 is employed as a pump, video, and optical heating focussing objective, while an optional lens L6 is used to focus the sampled light from BS5 onto the video camera 124.

Figure 1C:
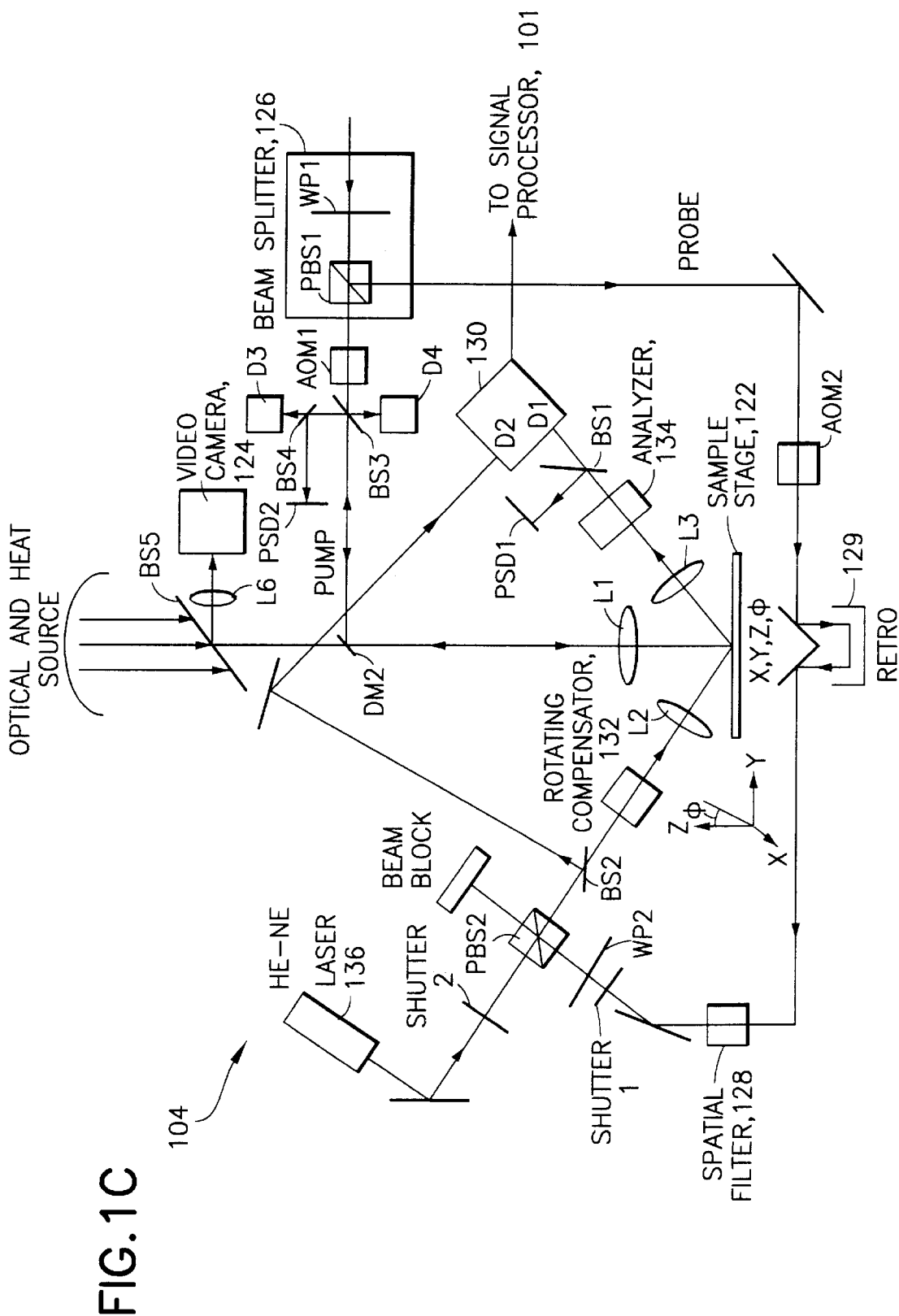
FIG. 1C is a block diagram of a third embodiment of an ultra-fast optical system that is suitable for use in practicing this invention, specifically, a single wavelength, normal pump, oblique probe, combined ellipsometer embodiment.

Reference is now made to FIG. 1C for illustrating an embodiment of apparatus 104, specifically a single wavelength, normal pump, oblique probe, combined ellipsometer embodiment. As before, only those elements not described previously will be described below.

Shutter 1 and shutter 2 are computer controlled shutters, and allow the system to use a He—Ne laser 136 in the ellipsometer mode, instead of the pulsed probe beam. For transient optical measurements shutter 1 is open and shutter 2 is closed. For ellipsometer measurements shutter 1 is closed and shutter 2 is opened. The HeNe laser 136 is a low power CW laser, and has been found to yield superior ellipsometer performance for some films.

Figure 1D:
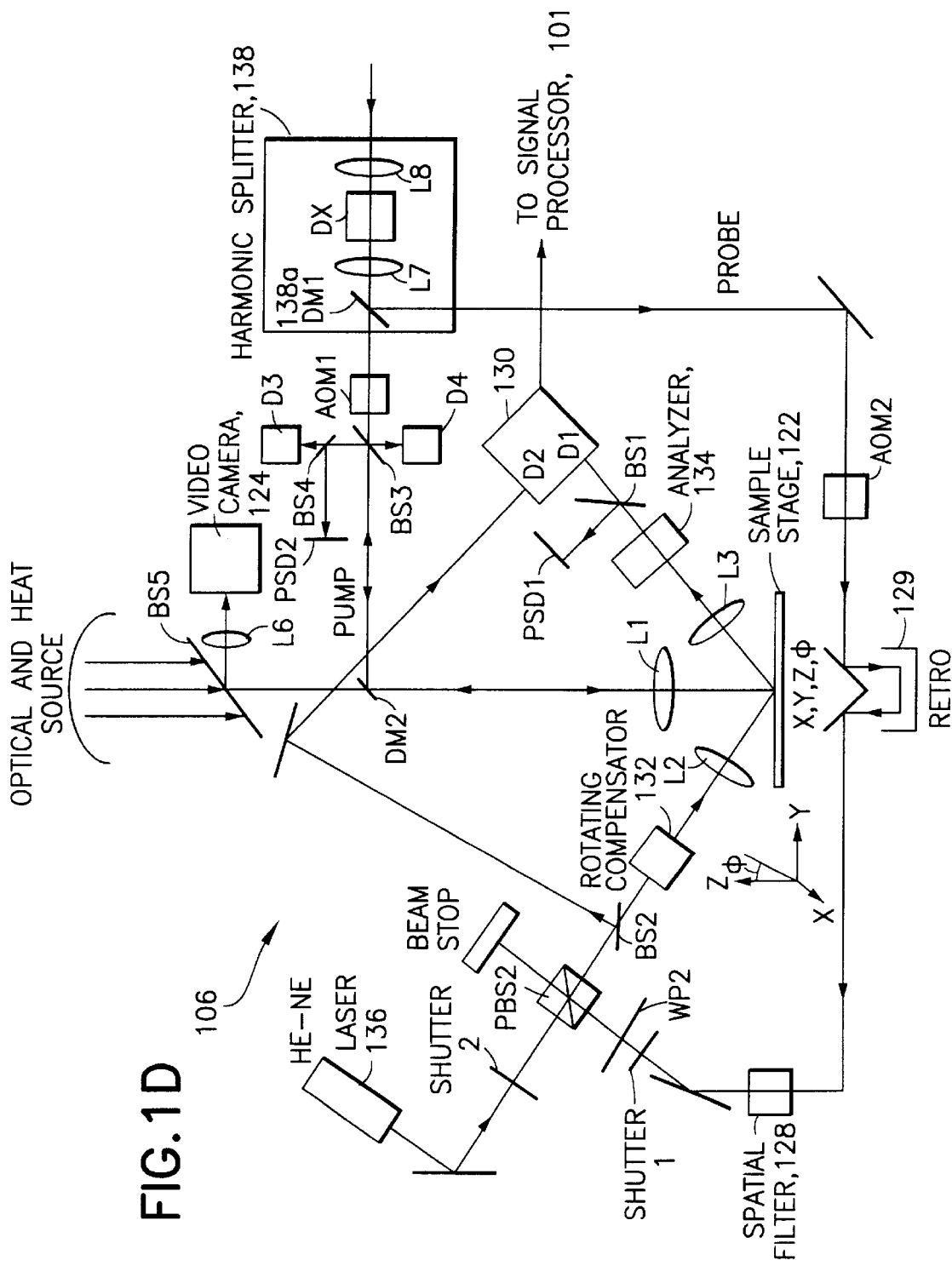
FIG. 1D is a block diagram of a fourth embodiment of an ultra-fast optical system that is suitable for use in practicing this invention, specifically, a dual wavelength, normal pump, oblique probe, combined ellipsometer embodiment.

FIG. 1D is a dual wavelength embodiment 106 of the system illustrated in FIG. 1C. In this embodiment the beamsplitter 126 is replaced by a harmonic splitter, an optical harmonic generator that generates one or more optical harmonics of the incident unsplit incident laser beam. This is accomplished by means of lenses L7, L8 and a nonlinear optical material (DX) that is suitable for generating the second harmonic from the incident laser beam. The pump beam is shown transmitted by the dichroic mirror (DM1 138*a*) to the AOM1, while the probe beam is reflected to the retroreflector. The reverse situation is also possible. The shorter wavelength may be transmitted, and the longer wavelength may be reflected, or vice versa. In the simplest case the pump beam is the second harmonic of the probe beam (i.e., the pump beam has one half the wavelength of the probe beam).

It should be noted that in this embodiment the AOM2 can be eliminated and instead a color filter F1 can be used in front of the detector D1 in order to reduce the amount of light reaching the detector D1. F1 is a filter having high transmission for the probe beam and the He-Ne wavelengths, but very low transmission for the pump wavelength.

Finally, FIG. 1E illustrates a normal incidence, dual wavelength, combined ellipsometer embodiment 108. In FIG. 1E the probe beam impinges on PBS2 and is polarized along the direction which is passed by the PBS2. After the probe beam passes through WP3, a quarter wave plate, and reflects from the sample, it returns to PBS2 polarized along the direction which is highly reflected, and is then directed to a detector DO in detector block 130. D0 measures the reflected probe beam intensity.

In greater detail, WP3 causes the incoming plane polarized probe beam to become circularly polarized. The handedness of the polarization is reversed on reflection from the sample, and on emerging from WP3 after reflection, the probe beam is linearly polarized orthogonal to its original polarization. BS4 reflects a small fraction of the reflected probe onto an Autofocus Detector AFD.

DM3, a dichroic mirror, combines the probe beam onto a common axis with the illuminator and the pump beam. DM3 is highly reflective for the probe wavelength, and is substantially transparent at most other wavelengths.

D1, a reflected He-Ne laser 136 detector, is used only for ellipsometric measurements.

It should be noted that, when contrasting FIG. 1E to FIGS. 1C and 1D, that the shutter 1 is relocated so as to intercept the incident laser beam prior to the harmonic splitter 138.

Figure 6:
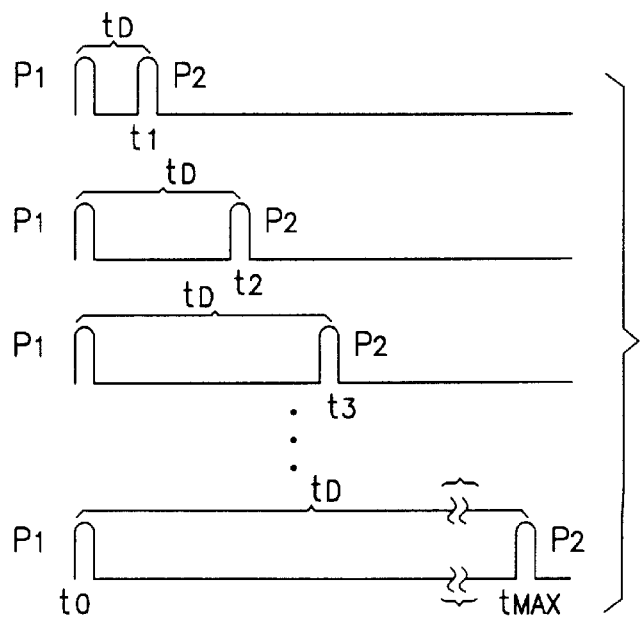
FIG. 6 illustrates a timed sequence of a plurality of consecutive pump pulses and corresponding probe pulses.

Based on the foregoing descriptions, a selected one of these presently preferred embodiments of measurement apparatus provide for the characterization of samples in which a short optical pulse (the pump beam) is directed to an area of the surface of the sample, and then a second light pulse (the probe beam) is directed to the same or an adjacent area at a later time. The retroreflector 129 shown in all of the illustrated embodiments of FIGS. 1A–1E can be employed to provide a desired temporal separation of the pump and probe beams. FIG. 6 illustrates various time delays ($t_D$) between the application of a pump beam pulse (P1) and a subsequent application of a probe beam pulse (P2), for times ranging from $t_1$ to $t_{MAX}$.

Figure 1F:
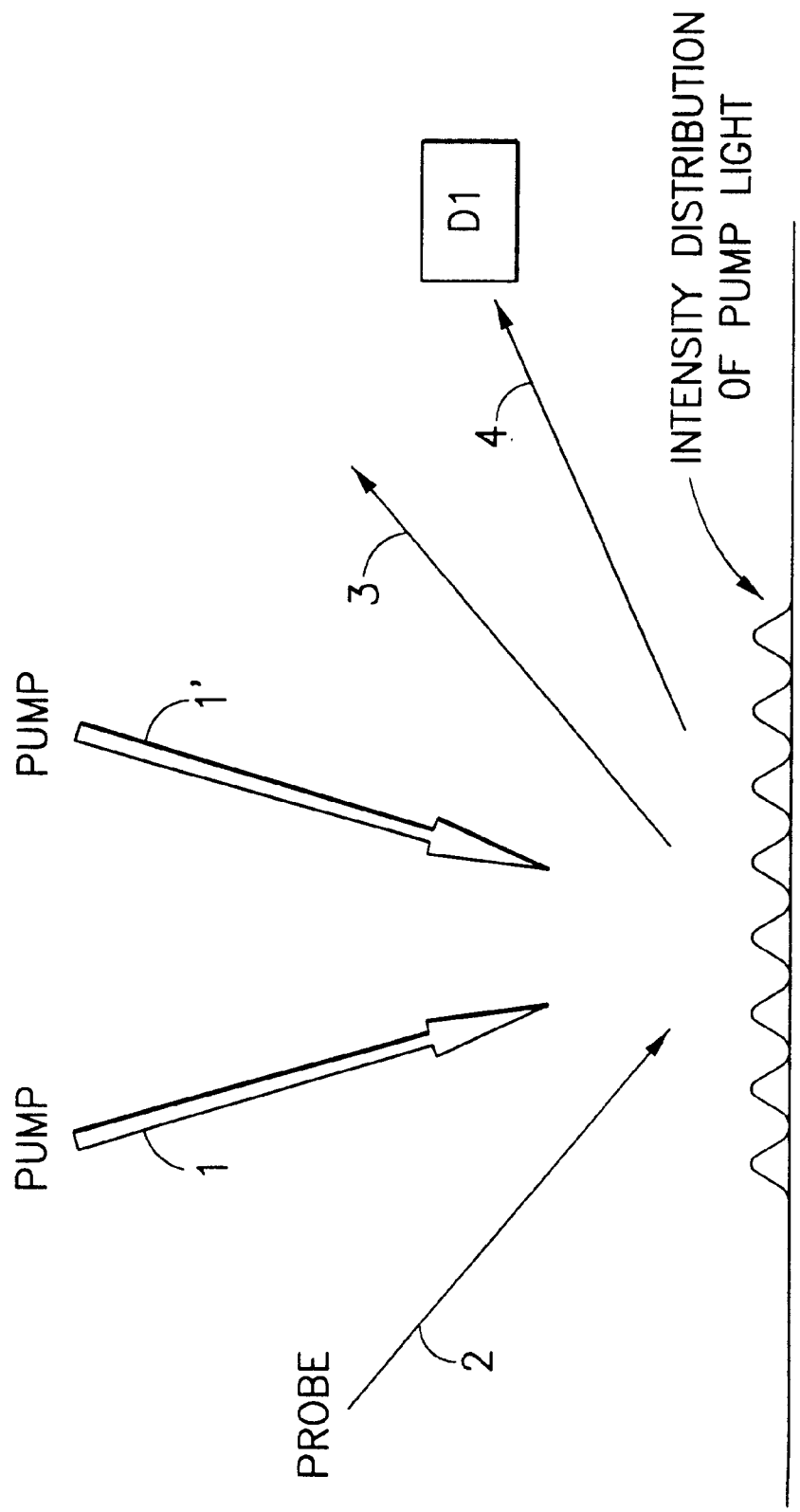
FIG. 1F illustrates the operation of a transient grating embodiment of this invention, wherein the pump pulse is divided and made to interfere constructively and destructively at the surface of the sample.

The five embodiments 100, 102, 104, 106 and 108, as described above, have in common the feature that a sequence of pump pulses are generated and directed at the free surface 18 of the sample 10 as shown in FIG. 4. Each pump pulse illuminates the same area of the sample 10 with an intensity that varies smoothly across the area. It is also within the scope of this invention to make measurements of the transient optical response by means of the induced transient grating method. (See: D. W. Phillion, D. J. Kuizenga, and A. E. Siegman, Appl. Phys. Lett. 27, 85 (1975)). To induce a transient grating each pump pulse is divided into two or more components by means of a beam splitter or beam splitters, these components then pass through separate optical paths, and are then all directed onto the same area of the surface of the sample. If the different components are directed onto the surface with different angles there will be places within the area where the different components interfere constructively and places where the interference is destructive. Thus the total intensity of the pump light will vary across the sample surface. In the case that only two components 1 and 1' are present, as shown in FIG. 1F, the intensity will vary periodically across the sample surface. The periodicity of the intensity, i.e. the spacing between successive points of maximum intensity, is determined by the wavelength of the pump light and the angles at which the different components of the pump light are incident onto the surface. Then the amount of light absorbed in the structure will vary periodically across the surface, and the propagating strain pulse generated by the pump light will vary periodically across the sample. Consequently, the transient changes in the optical properties of the top surface of the sample which result from the return of the strain pulse to the top surface will also vary periodically across the surface of the sample. This variation of the transient changes in the optical properties of the sample is equivalent to the production of a transient diffraction grating coinciding with the sample surface. When probe light 2 is incident on the area excited by the pump, a part 4 of the probe light will be diffracted, i.e. a part of the probe light will be reflected in a direction, or directions, away from the direction 3 of specular reflection. Measurement of the intensity of this diffracted probe light by means of the detector D1 as a function of the time delay t between the application of the pump and probe beams provides an alternate method for the characterization of the transient optical response produced in the sample.

Figure 2:
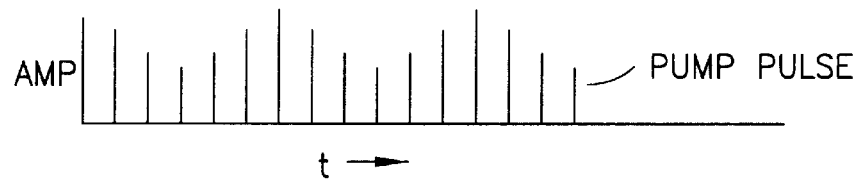
FIG. 2 illustrates a pulse train of pump beam pulses having an overlying low frequency intensity modulation impressed thereon.

Typical characteristics of the light pulses employed in the systems 100–108 of FIGS. 1A–1E are as follows. The pump pulse has an energy of approximately 0.001 to 100 Nj per pulse, a duration of approximately 0.01 psecs to 100 psec per pulse, and a wavelength in the range 200 nm to 4000 nm. The pulse repetition rate (PRR) is in the range of 100 Hz to 5 Ghz and, as is shown in FIG. 2, the pump pulse train may be intensity modulated at a rate of 1 Hz to 100 Mhz, depending on the PRR. The pump pulse is focussed to form a spot on the sample surface of diameter in the range of approximately 10 micrometers to 20 micrometers, although smaller spot sizes, and hence smaller lateral resolutions, can also be employed.

Figure 3A:
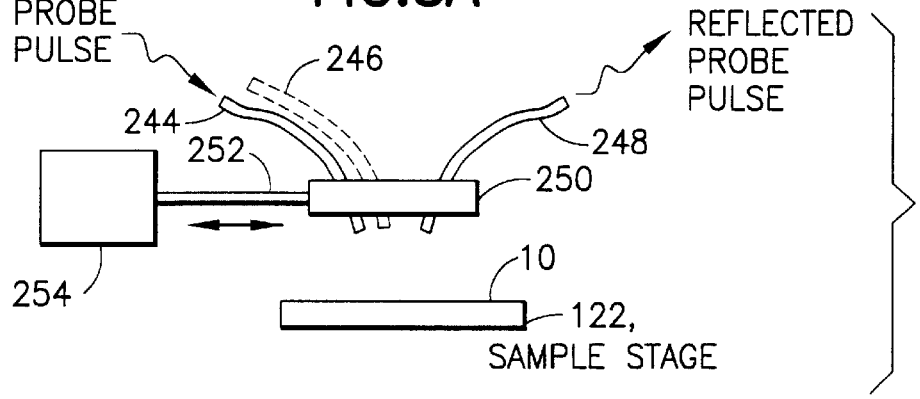
FIG. 3A illustrates a further embodiment wherein one or more optical fibers are positioned for delivering the pump beam and/or probe beam and for conveying away the reflected probe beam.

Referring to FIG. 3A, it is also within the scope of the teaching of this invention to deliver the pump pulse, or the probe pulse, or both the pump and probe pulses, through an optical fiber 244. Alternatively, a second input fiber 246 can be provided, whereby the pump pulse is delivered through the fiber 244 and the probe pulse is delivered through the fiber 246. Another fiber 248 can also be employed for receiving the reflected probe pulse and delivering same to the photodetector (not shown). For this embodiment the end of the optical fiber(s) are affixed to and supported by a holding stage 250. The holding stage 250 is preferably coupled through a member 252 to an actuator 254, such as a linear actuator or a two degree of freedom positioning mechanism. In this manner the reliability and repeatability of the measurement cycle is improved, in that the size and position of the focussed pump, probe, or pump and probe beams on the sample surface are independent of minor changes in the direction or profile of the laser output beams, or changes in the profile of the probe beam associated with the motion of any mechanical stage that may be used to effect the delay $t_D$. Preferably, the angular orientation between the end of the probe beam delivery fiber and the end of the reflected probe beam fiber is such as to optimize the gathering of reflected probe beam light from the sample surface. It is also within the scope of this invention to use one or more lenses following the fiber or fibers, in order to focus the output beams from the fibers onto the sample surface, or to collect the reflected probe light and to direct it into the fiber 248 of FIG. 3A.

Figure 3B:
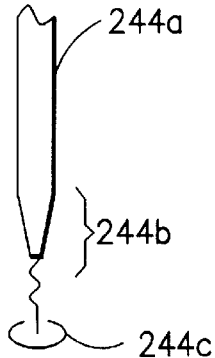
FIG. 3B illustrates a terminal end of a fiber optic that has been reduced in cross-sectional area for delivering an optical pulse to a small surface area of a sample.

FIG. 3B shows an embodiment wherein a terminal portion 244b of a pump and/or probe beam delivery fiber 244a is reduced in diameter, such as by stretching the fiber, so as to provide a focussed spot 244c having a diameter that is less than the normal range of optical focussing. When coupled with the embodiment of FIG. 3A this enables the pump and or probe optical pulse to be repeatably delivered to a very small region of the sample surface (e.g., to a spot having a diameter≦one micrometer), regardless of any changes that are occurring in the optical path length of the probe beam.

Figure 5:
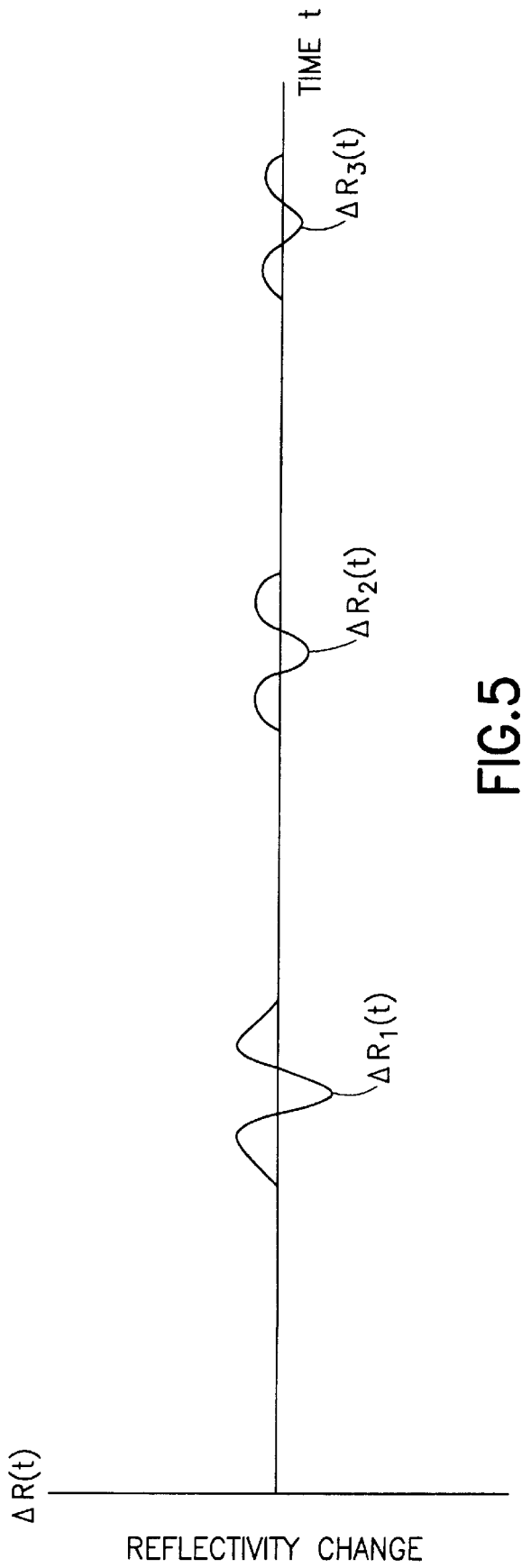
FIG. 5 is a graph relating the change in optical reflectivity ΔR(t) with respect to time t for the sample thin film.

The apparatus 100, 102, 104, 106 and 108, as described above, is capable of measuring the transient change in the reflectivity ΔR(t) of the probe beam as shown in FIG. 5. FIG. 5 graphically depicts the change in optical reflectivity ΔR(t) as a function of time. In FIG. 5, the time t since the application of the pump beam to the sample is plotted along the abscissa. The transient changes (i.e. echoes) in optical reflectivity $\Delta R_i(t)$ are plotted along the ordinate axis. Each transient change corresponds to a consecutive return of the propagating strain pulse to the surface of the film. By detecting the transient change in reflectivity ΔR(t) of the probe beam, the time interval τ corresponding to the round trip time of the stress pulse in the sample may be determined. The time interval τ for the round trip time of the stress pulse in the sample is, $$\tau = 2\frac{d}{v} \quad (4)$$

where d is the film thickness and v is the sound velocity. The time interval τ for the round trip time of the stress pulse in the sample is also coincident to the time between the application of the pump beam pulse and detection, by the apparatus 100, 102, 104, 106 and 108, of the change in optical reflectivity ΔR of the reflected probe pulse arising from the returning strain pulse. Thus, a determination of the time interval τ when there is an echo feature in ΔR(t) of the reflected probe beam (see FIG. 5) caused by the returning stress pulse can be used to find the round trip time of the stress pulse in the sample film.

Figure 7:
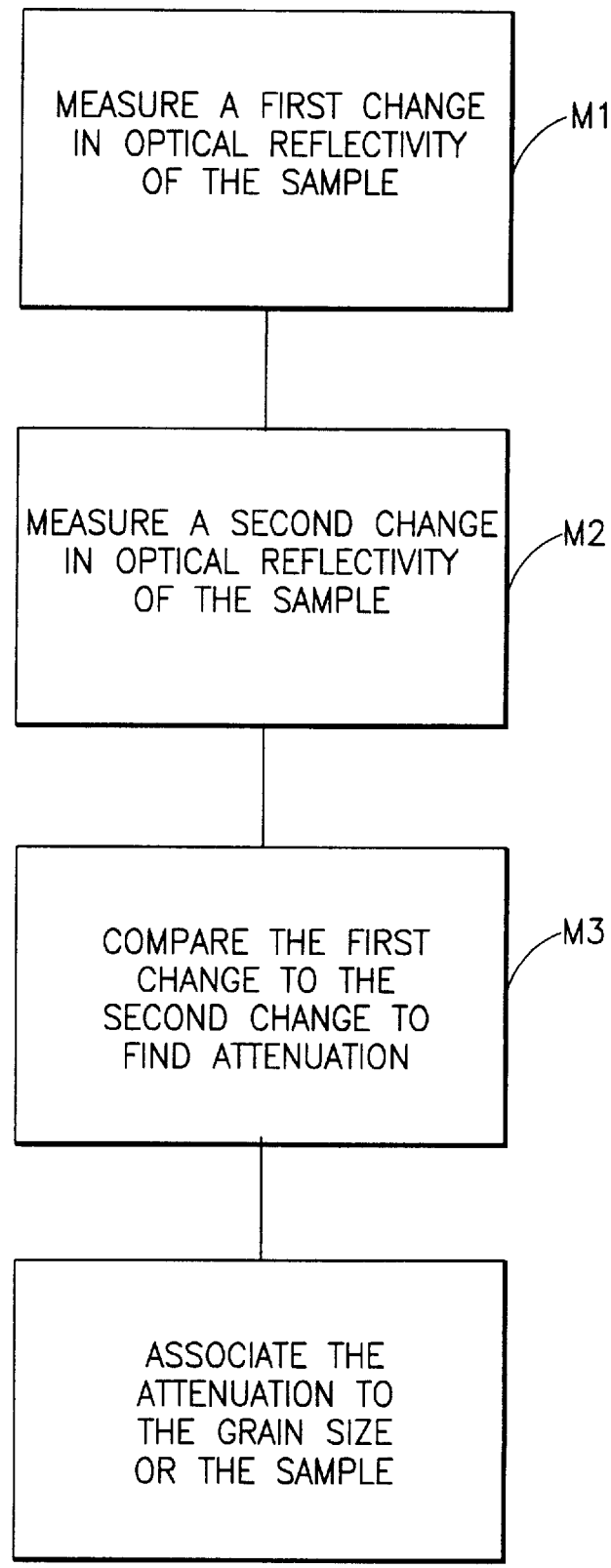
FIG. 7 is a flow chart depicting a method for finding the grain size in thin films in accordance with this invention.

The present invention allows the accurate determination of the grain size in the thin film. Referring now to FIG. 7, there is shown a flow chart diagrammatically depicting a first procedure for measuring the grain size of the thin film. In the first step M1, the shape of a first transient $\Delta R_1(t)$ in the optical reflectivity of the probe beam associated with the first return of the propagating strain pulse to the top surface of the film is measured by the apparatus 100, 102, 104, 106 and 108. The first transient $\Delta R_1(t)$ in optical reflectivity is recorded in processor 101. Next, in step M2, the shape of a second transient or echo $\Delta R_2(t)$ in the optical reflectivity of the probe beam associated with the second return of the propagating strain pulse to the top surface of the thin film is measured by the apparatus 100, 102, 104, 106 and 108. The second transient $\Delta R_2(t)$ in optical reflectivity is also recorded in the processor 101. In step M3, the first transient change $\Delta R_1(t)$ and the second transient change $\Delta R_2(t)$ in the optical reflectivity of the probe beam are compared by the processor 101 to find the attenuation α of the propagating strain pulse in the thin film. Finally, in step M4, the attenuation α of the strain pulse is associated by the processor 101 to a grain size of the thin film.

In order to relate the attenuation α of the propagating strain pulse to the grain size of the thin film, the attenuation α(f) should be found as a function of frequency f (see Eqs. 1 and 3). Hence, the shape of transient changes in optical reflectivity $\Delta R_1(t)$ and $\Delta R_2(t)$ of the probe beam which are measured as a function of time by the apparatus 100, 102, 104, 106 and 108 are converted to the frequency spectrum. This is done by taking the Fourier transforms $\Delta R_1(f)$ and $\Delta R_2(f)$ of these two echoes in optical reflectivity $\Delta R_1(t)$ and $\Delta R_2(t)$, using for example a fast Fourier transform program in conjunction with the digital processor 101 of the apparatus 100, 102, 104, 106 and 108. The attenuation α(f) of the propagating strain pulse as related to a single predetermined frequency $f_i$ can be found by comparing the first change in optical reflectivity $\Delta R_1(f_i)$ to the second change in optical reflectivity $\Delta R_2(f_i)$ at the frequency $f_i$. The attenuation α(f) as related to a range of frequencies $f_1$ to $f_2$ can be determined by making the above comparison between the first transient optical response $\Delta R_1(f)$ and second transient optical response $\Delta R_2(f)$ for the range of frequencies $f_1$ to $f_2$. The attenuation α(f) of the transients is determined by the processor 101 of the apparatus 100, 102, 104, 106 and 108.

Compared to the first transient change in optical reflectivity defined relative to frequency $\Delta R_1(f)$, the second transient change $\Delta R_2(f)$ is reduced as a result of the following two factors (see FIG. 5 which shows the reduction of the transient changes in optical reflectivity associated with subsequent returns of the propagating strain pulse). The first factor is that a fraction of the sound pulse will be transmitted from the film into the substrate each time the pulse reaches the film-substrate interface. As a result of this partial transmission the amplitude of the second echo will be reduced compared to the first echo by a factor equal to the acoustic reflection coefficient $r_{F-S}$ at the film-substrate interface. This reflection coefficient can be calculated theoretically from the acoustic impedances of the film and substrate. The acoustic impedance of a material is the product of the density and the sound velocity. The second factor which accounts for the rest of the attenuation $\alpha$ is due to the scattering of the sound by the anisotropic elastic properties of the grains as previously described. The combination of the two effects just mentioned gives the result:

$$\Delta R_2(f) = \Delta R_1(f) \, r_{FS} \exp[-2d\alpha(f)] \qquad (5)$$

Thus, from a measurement of the change in optical reflectivity $\Delta R_1(t)$ and $\Delta R_2(t)$ with respect to time converted to the frequency spectrum $\Delta R_1(f)$ and $\Delta R_2(f)$, the attenuation $\alpha(f)$ can be determined from the formula:

$$\alpha(f) = \frac{1}{2d} \ln\left( \frac{r_{FS} \Delta R_1(f)}{\Delta R_2(f)} \right) \qquad (6)$$

Hence, for a sample of a particular material with a known reflection coefficient $r_{FS}$ and a given thickness d, it is possible to determine the attenuation $\alpha(f)$ for a single frequency $f_1$ or over a frequency range from $f_1$ up to $f_2$. In order to make a reliable determination of $\alpha(f)$ at a particular frequency f it is desirable that the Fourier transforms $\Delta R_1(f)$ and $\Delta R_2(f)$ both be determined accurately.

Once the attenuation $\alpha(f)$ has been determined there are a number of approaches that can be used in order to find the grain size. In a first approach, a single frequency $f_3$ can be chosen such that the highest possible accuracy of the attenuation $\alpha(f_3)$ measurement is achieved. Thus, at the frequency $f_3$ both of the Fourier transforms $\Delta R_1(f_3)$ and $\Delta R_2(f_3)$ can be measured with high accuracy. The attenuation at frequency $f_3$ is then found from Eq. 6. The attenuation $\alpha(f_3)$ is then compared with the theoretical formulae (Eqs. 1 and 3) and the grain size determined. This determination is to be performed in a self consistent way. For example, it may first be supposed that $\lambda$ is greater than $2\pi D_{av}$ so that Eq. 1 applies. Then the grain size is determined from Eq. 1. If the resulting average grain diameter $D_{av}$ is such that the condition $\lambda > 2\pi D_{av}$ is satisfied, the result for $D_{av}$ is considered satisfactory. If the condition is not satisfied then it is necessary to use Eq. 3 to find the grain size.

In an alternate approach, Eq. 6 is used first to give the attenuation over the entire frequency range $f_1$ to $f_2$. This measured attenuation can then be compared to the attenuation calculated from Eqs. 1 and 3 based on an assumed grain size. Then the grain size is adjusted to achieve a best fit of the theoretical attenuation to the results of the measurement.

In another alternate approach, the Fourier transform $\Delta R_1(f)$ of the first echo $\Delta R_1(t)$ is calculated. A grain size is assumed and the frequency dependence of the attenuation $\alpha(f)$ is calculated from theory (see Eqs. 1 and 3). An expected form of the Fourier transform $\Delta R_2(f)$ is then calculated from Eq. 5. In this case, the change in optical reflectivity of the probe beam relative to frequency $\Delta R_1(f)$ is a measured quantity and $\alpha(f)$ is a theoretical value based on an assumed grain size. Then from $\Delta R_2(f)$ the expected form of the second echo $\Delta R_2(t)$ is calculated by means of a Fourier transform. This expected form is compared with the experimentally-measured result for $\Delta R_2(t)$. This procedure is then repeated for a series of trial grain sizes until a best fit to the experimental $\Delta R_2(t)$ is obtained.

The different approaches described above for determining the grain size of a thin film are based on the assumption that the preferential orientation of the grains in the thin film is small. If there is significant preferred orientation of the grains in the thin film, the attenuation will be reduced. Thus, for example, if there is preferred orientation an attempt to determine the grain size by comparing an attenuation measured at one frequency with Eq. 1 or Eq. 3 will give an incorrect result. The grain size that is obtained by the methods described above will be too small by a factor which increases with the degree of preferential orientation. However, as already described, the frequency $f_c$ at which there is a crossover from attenuation $\alpha(f)$ varying as $f^4$ (see Eq. 1) to $f^2$ (see Eq. 3) will still be related to the average grain size through the relation $\lambda = 2\pi D_{av}$. Provided the frequency range $f_1$ to $f_2$ over which accurate measurements of the attenuation can be made includes this crossover frequency, this crossover frequency $f_c$ can be determined. The result for the crossover frequency $f_c$ can then be used to determine the grain size. Once the grain size is determined, the degree of preferred orientation can be estimated by comparison of the measured attenuation at one or more frequencies with the appropriate theoretical expressions Eqs. 1 and 3, these expressions having been modified for the effects of preferred orientation. Thus the degree of preferred orientation is adjusted so that the theoretical attenuation matches the experimentally measured values.

In the preferred method of this invention, the comparison performed in step M3 of FIG. 7 is performed between the first transient change in optical reflectivity $\Delta R_1(t)$ of the probe beam and the second transient change $\Delta R_2(t)$ measured by the apparatus 100, 102, 104, 106 and 108. In an alternate method of this invention, the comparison in step M3 can be performed between any initial transient change in optical reflectivity $\Delta R_i(t)$ (i.e. the first, second or third echo in optical reflectivity of the probe beam) and any subsequent transient change $\Delta R_{i+m}(t)$ (see FIG. 5) measured by the apparatus 100, 102, 104, 106 and 108 or by the transient grating method previously described. The two transient changes in optical reflectivity may be consecutive (e.g. $\Delta R_i(t)$ and $\Delta R_{i+1}(t)$) or non-consecutive (e.g. $\Delta R_i(t)$ and $\Delta R_{i+m}(t)$ where $m \geq 2$). In the case where the two transient changes being compared are non-consecutive (i.e. $m \geq 2$), the expression in Eq. 6 becomes:

$$\alpha(f) = \frac{1}{2md} \ln\left( \frac{r_{FS}^m \Delta R_i(f)}{\Delta R_{i+m}(f)} \right) \qquad (7)$$

Hence, the attenuation $\alpha(f)$, and thus the grain size of the thin film can be determined from any two transient changes in optical reflectivity of the probe beam measured by the apparatus 100, 102, 104, 106 and 108.

In another alternate method of this invention, the second echo $\Delta R_2(t)$ may be too small for accurate measurements of its amplitude. This may result from a large attenuation in the film or from a very small reflection coefficient at the interface between the film and the substrate. Under these conditions measurements can be made by the following method. A calculation can be performed of the expected shape of the first echo in an ideal sample in which there is no attenuation of the strain pulse due to the scattering by elastic anisotropy of grains. By comparison of this theoretical echo shape with the echo shape measured in the sample the attenuation can be determined over some frequency range.

The processor 101 of the apparatus 100, 102, 104, 106 and 108 is programmed accordingly to incorporate one or more of the above described approaches for determining the grain size of the sample from the attenuation of the transient optical responses detected by the apparatus 100, 102, 104, 106 and 108. Before using the apparatus 100, 102, 104, 106 and 108 to measure the grain size of the sample, it is desirable to calibrate the apparatus using a test sample having a known grain size.

In yet another alternate method of this invention, when it is desirable to make rapid measurements on a series of films of the same material, a comparison method may be used. In this method, the shape of one particular echo (e.g. the first echo) is measured in a series of calibration samples of known grain size. The results on the sample film are then compared with the measurements on the calibration samples in order to determine the grain size. It may be advantageous to extend this method by measurement of two more echoes in the calibrated samples, and in the sample film.

The above descriptions apply to the use of the invention to measure the grain size of a single thin film which has been deposited onto a substrate. The invention can also be applied to the measurement of the grain size of individual films in more complex structures or stack consisting of a number of thin films deposited as a sequence on top of a substrate. Some of the films in the stack may be transparent and some optically absorbing. As a consequence, the light of the pump pulse will be strongly absorbed in some of the films and weakly absorbed or not absorbed at all in other of the films. Strain pulses will be generated within each of the films in which light is absorbed. The strain pulses will propagate through the structure and will be partly reflected and partly transmitted at each interface that is encountered. The change in optical reflectivity $\Delta R(t)$ of the stack contains features or components (i.e. echoes in the change in optical reflectivity $\Delta R(t)$, see FIG. 5) arising from the propagation of strain pulses through the various films in the stack. From these features in the change in optical reflectivity $\Delta R(t)$, the attenuation of strain pulses propagating within the different films making up the stack structure can be determined. To measure the attenuation of the strain pulse propagating in a particular film, the component of the change in optical reflectivity $\Delta R(t)$ corresponding to the propagating strain pulse in that film is identified. To make this identification, it is desirable to perform a computer simulation the results of which are compared with the measured change in optical reflectivity $\Delta R(t)$ of the stack structure. In the computer simulation, the propagation of strain pulses through the structure is calculated taking account of the various acoustic reflections that take place at the interfaces between the different film layers. From the calculated strain distribution in the structure, the change $\Delta R(t)$ in optical reflectivity corresponding to the transit time of a strain pulse through the particular film layers in the sample is then calculated. In this calculation, it is an advantage if the index of refraction of some, or all of the films has been previously determined through ellipsometric measurements. The ellipsometer mode of apparatus 102 described previously (see FIG. 1B) is used to measure the index of refraction of the particular films. The parameters of the structure (e.g. the thickness of the different films) are then adjusted so as to give a best fit between the calculated and measured change in optical reflectivity $\Delta R(t)$. Once the parameters of the structure are determined, then the transit time through a particular film in the sample is found, and from the transit time the component of the change in optical reflectivity $\Delta R(t)$ corresponding to the strain pulse propagating in a particular film is identified. After the component of the change in optical reflectivity corresponding to the strain pulse in a particular film is identified, then the attenuation of the strain pulse is measured as described previously with reference to FIG. 7. From the attenuation of the strain pulse in a particular film the grain size in that film can be determined. In addition, this invention can be applied to the measurement of the grain size in films which are included in laterally-patterned structures.

It is also within the scope of the invention to measure the grain size of a sample by measuring other transient optical properties instead of the change in the optical reflectivity. As previously mentioned, the apparatus 100, 102, 104, 106 and 108, as shown in FIGS. 1A–1E, are capable of measuring the (1) transient change in the reflectivity $\Delta R(t)$ of the probe beam. With suitable modifications the apparatus can be used to measure (2) the change $\Delta T$ in the intensity of the transmitted probe beam, (3) the change $\Delta P$ in the polarization of the reflected probe beam, (4) the change $\Delta \phi$ in the optical phase of the reflected probe beam, and/or (5) the change in the angle of reflection $\Delta \beta$ of the probe beam. These quantities may all be considered as transient responses of the sample which are induced by the pump pulse. These measurements can be made together with one or several of the following: (a) measurements of any or all of the quantities (1)–(5) just listed as a function of the incident angle of the pump or probe light, (b) measurements of any of the quantities (1)–(5) as a function of more than one wavelength for the pump and/or probe light, (c) measurements of the optical reflectivity through measurements of the incident and reflected average intensity of the pump and/or probe beams; (d) measurements of the average phase change of the pump and/or probe beams upon reflection; and/or (e) measurements of the average polarization and optical phase of the incident and reflected pump and/or probe beams. The quantities (c), (d) and (e) may be considered to be average or static responses of the sample to the pump beam.

It is also within the scope of the invention to make measurements on films which are so thin that the spatial extent of the generated strain pulse (in the direction normal to the plane of the film) is comparable to the thickness of the film. For such films it is not useful to consider that the generated strain pulse bounces back and forth within the sample. Instead, one should consider that the pump pulse excites the film into its fundamental vibrational thickness mode of frequency f. Under these conditions the change in optical reflectivity $\Delta R(t)$ will vary periodically with the time t. The period of this vibration is the period of the fundamental vibrational thickness mode. The rate of damping of the mode gives the attenuation at the frequency f.

Therefore, while the invention has been particularly shown and described with respect to preferred embodiments thereof, it will be understood by those skilled in the art that changes in form and details may be made therein without departing from the invention. Accordingly, the present invention is intended to embrace all such alternatives, modifications and variances which fall within the scope of the appended claims.

What is claimed is:

1. A method for determining grain size in a sample, the method comprising the steps of:

inducing a propagating disturbance in the sample by an application of at least one pulse of electromagnetic energy to the sample from a pump beam;

measuring a first change in optical response of the sample to a pulsed probe beam by measuring a change $\Delta\phi$ in optical phase of a portion of the probe beam;

measuring a second change in optical response of the sample to the pulsed probe beam by measuring the change $\Delta\phi$ in optical phase of the portion of the probe beam, the second change in optical response being time delayed from the first change in optical response of the sample;

comparing the first change in optical response of the sample to the second change in optical response of the sample to determine an amount of attenuation of the propagating disturbance in the sample; and associating the amount of attenuation of the propagating disturbance in the sample with a grain size of the sample.

2. A method as in claim 1, wherein the step of comparing comprises comparing the first change in optical response to the second change in optical response at a predetermined frequency.

3. A method as in claim 1, wherein the step of comparing comprises comparing the first change in optical response to the second change in optical response for a predetermined range of frequencies.

4. A method as in claim 1, wherein the sample is comprised of at least one thin film of between about 100 Å and about 10$\mu$ in thickness, the at least one thin film being disposed on a substrate.

5. A method as in claim 1, wherein the sample is comprised of a metal-containing film.

6. A method as in claim 1, wherein the sample is comprised of a film that is comprised of copper.

7. A method as in claim 1, wherein the sample is comprised of a film that is comprised of aluminum.

8. A method as in claim 1, wherein at least the step of measuring the first change in optical response comprises the steps of:

applying a sequence of pump pulses to the sample for inducing a spatially varying strain pulse in the sample; and applying a sequence of probe pulses to the sample for interacting with the strain pulse in the sample.

* * * * *